United States Patent
Clokie

(10) Patent No.: US 6,309,659 B1
(45) Date of Patent: Oct. 30, 2001

(54) REVERSE PHASE CONNECTIVE TISSUE REPAIR COMPOSITION

(75) Inventor: Cameron M. L. Clokie, Rancho Palos Verdes, CA (US)

(73) Assignee: GenSci OrthoBiologics, Inc., Irvine, CA (US)

( * ) Notice: Subject to any disclaimer, the term of this patent is extended or adjusted under 35 U.S.C. 154(b) by 0 days.

(21) Appl. No.: 08/922,068

(22) Filed: Sep. 2, 1997

(51) Int. Cl.[7] .............. A61F 13/00; A61F 2/00; A61K 9/14
(52) U.S. Cl. .............. 424/422; 424/433; 424/423; 424/426; 424/484
(58) Field of Search .................. 424/422, 433, 424/484, 423, 426

(56) References Cited

U.S. PATENT DOCUMENTS

| | | | |
|---|---|---|---|
| 4,394,370 | * 7/1983 | Jefferies | 606/76 |
| 4,472,840 | * 9/1984 | Jefferies | 623/16 |
| 5,073,373 | 12/1991 | O'Leary et al. | |
| 5,284,655 | 2/1994 | Bogdansky et al. | 424/422 |
| 5,290,558 | 3/1994 | O'Leary et al. | 424/422 |
| 5,356,629 | * 10/1994 | Sander et al. | 424/422 |
| 5,503,558 | 4/1996 | Clokie | 433/173 |
| 5,520,923 | 5/1996 | Tjia et al. | |
| 5,702,695 | 12/1997 | Clokie | 424/78.08 |
| 5,707,962 | * 1/1998 | Chen et al. | 514/12 |
| 5,733,868 | * 3/1998 | Peterson et al. | 514/2 |
| 6,030,635 | 2/2000 | Gertzman et al. | |

FOREIGN PATENT DOCUMENTS

| | | |
|---|---|---|
| 0 551 626 A1 | 7/1993 | (EP) . |
| 0 884 052 A1 | 12/1998 | (EP) . |
| 884052 | * 12/1998 | (EP) . |
| WO 95/13099 | 5/1995 | (WO) . |
| WO 97/18829 | 5/1997 | (WO) . |

OTHER PUBLICATIONS

Schmolka, "A Review of Block Polymer Surfactants", *J. Am. Oil Chemists Soc.* 54:110–116 (1977).

Schmolka, "A Comparison of Block Polymer Surfactant Gels", *J. Am. Oil Chemist Soc.* 68:206–209 (1991).

* cited by examiner

*Primary Examiner*—Michael G. Hartley
*Assistant Examiner*—Michael A. Willis
(74) *Attorney, Agent, or Firm*—Howrey Simon Arnold & White, LLP

(57) ABSTRACT

A biocompatible connective tissue repair composition which comprises a therapeutic material and a carrier comprising a means for achieving reverse phase characteristics, and methods for using said composition. The therapeutic material can be demineralized bone powder, and the carrier can be a poloxamer such as poloxamer 407.

7 Claims, No Drawings

REVERSE PHASE CONNECTIVE TISSUE REPAIR COMPOSITION

FIELD OF THE INVENTION

This invention concerns prosthetic materials. More particularly, it concerns a biocompatible material that exhibits reverse phase behavior.

BACKGROUND ART

Osteogenic bone repair materials are known in the art. These materials contain an osteogenic material, such as demineralized bone powder in a carrier, such as glycerol. See, e.g., U.S. Pat. No. 5,290,558, issued Mar. 1, 1994 to O'Leary et al., and U.S. Pat. No. 5,284,655, issued Feb. 8, 1994 to Bogdansky et al.

The carrier of the bone material in the art is a liquid, having a viscosity generally somewhere between runny to paste-like. "Runny" bone repair compositions have the advantage of being relatively easy to apply to and fill a bone defect, however, they are disadvantageous in that the material also tends to readily flow from the defect site. Conversely, bone repair compositions with a "paste-like" consistency are harder to apply to a defect, yet tend to remain positioned at the defect once applied. Additionally, when any of the bone repair compositions in the art are placed in vivo and become warmed, they become even less viscous; the decrease in viscosity is due to the addition of thermal energy to the composition.

Accordingly, there is a need for a bone repair composition that is easy to apply to a defect site, and which remains positioned at the site once placed at the site.

DISCLOSURE OF THE INVENTION

Disclosed is a biocompatible composition to facilitate repair of connective tissues. The composition can comprise demineralized bone powder, and, a carrier comprising a means for achieving reverse phase thermodynamic characteristics when mixed with the bone powder. The composition can be substantially liquid at 0° C., and substantially more viscous at 35° C., such that the composition has a consistency like that of paste floor wax or like solid shoe wax. The means for achieving reverse phase characteristics can comprise a block copolymer, such as a poly(oxyalkylene) block copolymer, which can be a poly(oxyethylene)-poly(oxypropylene)-poly(oxyethylene) triblock copolymer. The triblock copolymer can be a compound of the formula:

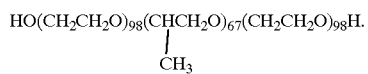

The means for achieving reverse phase characteristics comprises a poloxamer, such as poloxamer 407. The block copolymer can be a solid dispersed in a biocompatible solvent such as sterile water.

Preferably, the composition comprises a carrier of 25 weight percent of a block copolymer dispersed in 75 weight percent of a biocompatible solvent. To vary the consistency of the composition, the weight percentage of demineralized bone powder or other solid can be varied relative to the weight percentage of the carrier in the composition. For example, a paste-like form of the composition comprises 50 weight percent of bone powder and 50 weight percent of a carrier. A gel-like embodiment of the composition comprises 30 weight percent of bone powder and 70 weight percent of a carrier.

The bone powder of the composition can comprise particles with a median length to a median thickness ratio of about 1.742:1, a mean length of 0.25–1 mm (250–1,000 microns), and a mean thickness of about 0.5 mm (500 microns).

Also disclosed is a method to facilitate the development of bone tissue, said method comprising: providing a biocompatible connective tissue repair composition comprising demineralized bone powder, and, a carrier comprising a means for achieving reverse phase thermodynamic characteristics when mixed with the bone powder; and, placing the composition in a bony defect of a mammal. A prosthetic object can also be placed in the bony defect. The method can also comprise coating a portion of the prosthetic object with the biocompatible composition, and in this embodiment the step of placing the composition and the step of placing a prosthetic object can be contemporaneous.

MODES FOR CARRYING OUT INVENTION

Definitions

By "reverse phase" or "reverse thermal behavior" is intended a material that exhibits a physical property of becoming more viscous or solidified upon addition of thermal energy. It is believed that the solidification occurs by a mechanism other than that due to evaporation and corresponding loss of liquid.

As used herein, "ambient temperature" is 25° C., plus or minus 5° C.

As used herein, "body temperature" is 37° C., plus or minus 5° C.

As used herein, a "bony defect" or "bone defect site" is bony environment of a mammal which comprises some viable bone tissue. The defect can be congenital, caused by trauma, or caused by disease.

"Osteoinductive" materials cause undifferentiated cells to differentiate into a committed bone cell lines.

"Osteoconductive" materials provide support for cells of a bone cell lineage, e.g., permitting cells of a bone cell lineage to grow along or through a matrix or lattice.

Preferred Modes

In a preferred embodiment, the composition of the present invention is a flowable liquid when applied to a bony defect, whereupon the composition becomes increasingly solidified or viscous as it warms to ambient temperature and is further solidified as it warms to body temperature. Upon being warmed to body temperature, a preferred composition of the invention is a solid or highly viscous fluid. The reverse phase compositions in accordance with the invention are significantly different in principle from bone repair materials in the art, and do not function in the same way.

The composition comprises a therapeutic material for treating one or more connective tissues; and, a carrier. The therapeutic material can be a material to facilitate repair of connective tissues, i.e., a "connective tissue repair material." The carrier achieves reverse phase characteristics when mixed with the therapeutic material.

The therapeutic material can be a material that is osteoinductive, osteoconductive, or a material that is osteoinductive and osteoconductive. The therapeutic material can be xenogeneic, allogeneic, or autogenic. The therapeutic material can be alloplastic. As appreciated by one of ordinary skill in the art, the therapeutic material can comprise combinations of various therapeutic materials.

Examples of osteoinductive material include but are not limited to bone powder (mineralized or demineralized), tissue growth factor beta (TGF-β) types 1 through 13, bone morphogenetic protein (BMP) types 1 through 15, or combinations thereof.

Examples of therapeutic materials that are osteoconductive include but are not limited to xenogeneic bone (mineralized or demineralized); the xenogeneic bone can also be subjected to deproteination. Presently preferred xenogeneic sources are porcine and bovine.

Therapeutic materials that are osteoinductive and osteoconductive include particulate human allograft, e.g., of demineralized bone.

Examples of alloplastic materials comprise gypsum, coralline hydroxyapatite, synthetic hydroxyapatite, calcium carbonate, calcium phosphate, calcium sulfate, biodegradable polymeric materials, or combinations thereof.

A presently preferred composition comprises demineralized osteogenic bone powder in a carrier; the composition can be applied to a bone defect site to induce new bone growth. This composition of the present invention comprises demineralized bone particles or granules (referred to herein as "demineralized bone powder") in an inert biocompatible carrier.

In a preferred embodiment, the particles/granules have a median length to median thickness ratio about 1.742:1, a mean length of 0.25–1 mm (250–1,000 microns) and a mean thickness of about 0.5 mm (500 microns).

The presently preferred biocompatible carrier of the composition of the invention is a material that confers reverse phase thermodynamic properties on the composition. The use of PLURONIC® F127 as a component of an osteointegration promoting composition is set forth in U.S. Pat. No. 5,503,558, issued Apr. 2, 1996 to the inventor herein, Cameron M. L. Clokie; and in PCT International Publication No. WO 95/13099. In a presently preferred embodiment, the carrier comprises a polymer marketed by BASF (Parsipanny, N.J.) as PLURONIC® F127. PLURONIC® F127 is a poly(oxyalkylene) block copolymer; more specifically, a poly(oxyethylene)-poly(oxypropylene)-poly(oxyethylene) triblock copolymer; it is a member of a class of compounds called poloxamers. (Schmolka, "A Review of Block Polymer Surfactants" *J. Am. Oil Chemists Soc.* 54:110–116 (1977)). Several members of the poloxamer family exhibit reverse phase thermodynamic characteristics. PLURONIC® F127 is also known by the name "poloxamer 407." (Schmolka, "A Comparison of Block Polymer Surfactant Gels" *J. Am. Oil Chemist Soc.* 68:206–209 (1991)). PLURONIC® F127 has an average molecular weight of approximately 12,500. (Schmolka, "A Comparison of Block Polymer Surfactant Gels" *J. Am. Oil Chemist Soc.* 68:206–209 (1991)) The structure of the PLURONIC® F127 polymer is depicted as follows:

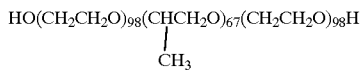

In preferred embodiments of a composition of the present invention, the carrier is a liquid diluted in a solvent or is a solid dispersed in a solvent. In one embodiment, PLURONIC® F127 is dispersed in a solvent such as sterile water. The PLURONIC® F127 carrier is vastly different in size, molecular weight, and chemical structure than carriers in the art. The carrier is also substantially different in terms of its functional properties than any carrier of a bone repair material in the art.

The proposed composition has a unique physical property, being flowable at refrigerated temperatures and increasingly solidified at elevated temperatures, such as ambient and body temperatures. This property is referred to in the art as "reverse phase" or "reverse thermal behavior". Due to the reverse phase property of the proposed composition, the composition is generally manufactured at refrigerated temperatures, such as 5° C. Manufacturing is done at refrigerated temperatures to enhance mixing of the components of the composition, since the proposed composition comprising an aqueous colloidal suspension of PLURONIC® F127 begins to become more viscous at ambient temperature, and is increasingly viscous and solidified at body temperature. Generally, a composition of the invention will be twice as viscous at 35° C. as it is at 0° C.

For example, the preferred PLURONIC® F127 carrier in the composition of the present invention (when dispersed in an appropriate amount of sterile water), has the unique property of being a liquid at refrigerated temperature and increasingly solidified, then solid at elevated temperature, absent the effects of evaporation and concomitant loss of water. This property is called "reverse phase" or "reverse thermal behavior" because it is the exact opposite of the thermodynamic properties exhibited by standard carriers.

It is believed that the reverse phase property is due, at least in part, to the fact that PLURONIC® F127 is composed of discrete blocks of both hydrophilic (i.e., oxyethylene) and hydrophobic (i.e., oxypropylene) subunits. (See e.g., Schmolka, "A Comparison of Block Polymer Surfactant Gels" *J. Am. Oil Chemist Soc.* 68:206–209 (1991)).

In contrast, standard carriers, as well as all liquids, manifest the typical physical property of becoming increasingly flowable upon addition of thermal energy, such as occurs when the liquid is heated to body temperature. However, the preferred carrier in a composition of the present invention becomes less flowable as energy is added to it either by heating or by shaking.

The unique reverse phase thermodynamic properties of the composition of the present invention allow the product to function in a substantially different, and preferred manner relative to other flowable bone repair products. When applied to a bone defect site, the reverse phase property of the preferred carrier provides support characteristics for the composition which are substantially different than the characteristics of standard carriers. Enhanced support is provided by the composition of the invention. The preferred PLURONIC® F127 carrier of the composition of the present invention helps to provide support characteristics which are unlike those of any standard carrier. This is because the composition is flowable at refrigerated temperature and can thus readily be applied to a bony defect site, but it becomes increasingly viscous and solidified once it is warmed at the site. The solidification of the composition of the present invention achieves several; beneficial effects. When solidified, the composition does not flow away from the defect site, and the solidified product immediately augments and facilitates structural support at the defect. Also, since the osteogenic composition of the invention is initially liquid, it readily fills a defect, then becomes solidified and achieves enhanced osteogenesis. Moreover, with preferred compositions of the invention, comprising a sterile aqueous colloidal suspension of PLURONIC® F127 as carrier and demineralized bone powder, the carrier will resorb or dissolve after about three days, leaving the osteogenic bone powder at the bone defect site. It is believed to be advantageous that the carrier disperses as this then allows for enhanced ingrowth of connective or vascular tissues.

In a composition of the invention, the weight percentages of the therapeutic material and the carrier can each be varied.

For example, the weight percent of the therapeutic material can vary between about 20 to 80 weight percent of the composition, and the weight percent of the carrier can vary between about 20 to 80 weight percent of the composition. Furthermore one or more additional components can be present in a composition of the invention, such as antibiotics, analgesic, anti-inflammatory agents, or agents to promote development of connective or circulatory system tissues.

EXAMPLES

Example 1

To obtain a composition having a gel-like consistency, the composition comprised 70 weight percent of a colloidal suspension of PLURONIC® F127 and 30 weight percent of bone powder. In this example, the carrier comprised 25 weight percent of PLURONIC® F127 powder dispersed 75 weight percent sterile water.

A composition of the invention is available as Dyna-Graft™ Gel (GenSci Regeneration Laboratories, Inc., Irvine, Calif.); this product is a composition comprising demineralized allograft bone from a single donor mixed with an inert preservative and a biocompatible carrier. The composition has a "gel" consistency and is provided in a sterile, single patient use package.

The tissues used in the bone repair composition are recovered by United States tissue banks, from carefully screened donors, according to standards established by the American Association of Tissue Banks. All such tissues meet stringent specifications during donor screening and laboratory testing in order to reduce the risk of transmitting any infectious disease.

For example, each donor is tested and found to be negative for (at a minimum): hepatitis B surface antigen, human immunodeficiency virus 1 and 2 antibodies, HTLV-1 antibody, hepatitis C virus antibody, and syphilis. The tests were performed by a CLIA approved laboratory utilizing FDA-licensed test kits. The medical and social history of the donor revealed no risk factors for, or clinical evidence of, HIV or hepatitis infection.

This biocompatible composition in accordance with the invention was produced under environmentally controlled conditions using stringent cleaning, preservation, and sterilization procedures. All steps are rigorously quality controlled in accordance with accepted methodologies in the art.

DynaGraft™ Gel is indicated for use in surgical procedures in which osteogenesis, calcification or bony fusion is needed to achieve or enhance the quality of the final result. Accordingly, DynaGraft™ Gel can be used in a variety of orthopedic, reconstructive, and dental bone grafting procedures. DynaGraft™ Gel may be used alone as a bone graft in cases in which the graft is not intended to provide weight bearing support or dimensional integrity to the graft site. If the graft is intended to be weight bearing, the composition should be used with appropriate fixation. DynaGraft™ Gel can, therefore, be used as a complement to musculoskeletal implants such as joint replacement prostheses, intraoral implants, and internal and external fixation devices for procedures in which demineralized freeze-dried bone allograft would be used.

The composition is sterilized by a targeted 2.5 megarads of electron beam irradiation as terminal sterilization. When implanting the composition, sterile technique should be maintained to minimize the risk of post-operative complications. Use of the composition is contraindicated when there is active or latent infection at or near the surgical site.

The composition should be stored long-term in a clean, dry place at room temperature. It should be kept out of direct sunlight and should not be frozen. DynaGraft™ Gel does not require rehydration prior to use.

The packaging of all DynaGraft™ implant compositions has been specially designed to provide ease of use within the surgical field. For example, the composition can be packaged within syringes that are kept sterile within one or more foil containers. DynaGraft™ Gel is supplied in 1.0 cc, 5 cc, and 10 cc syringes.

To use the composition packaged in syringes within foil containers, the packaging is opened by peeling open the outer foil and, using sterile technique, transferring the entire inner package to the sterile field. The inner package is then opened and the syringe removed. Immediately before use, a protective cap which covers the tip of the syringe is removed. The composition is then extruded by pushing on the syringe plunger to deliver the desired volume. Appropriate placement and/or fixation are critical factors in the avoidance of potentially adverse effects on product service life.

Accordingly, the DynaGraft™ Gel is bacteriologically sterile during the stated shelf life in an unopened and undamaged package. The product must be used before the expiration date. Unused product should be properly discarded.

Example 2

To obtain a composition having a paste-like consistency, the composition comprised 50 weight percent of a colloidal suspension of PLURONIC® F127 and 50 weight percent of bone powder. In this example, the carrier comprised 25 weight percent of PLURONIC® F127 powder dispersed in 75 weight percent sterile water.

A composition of the invention is available as Dyna-Graft™ Putty (GenSci Regeneration Laboratories, Inc., Irvine, Calif.); this product is a composition comprising demineralized allograft bone from a single donor mixed with an inert preservative and a biocompatible carrier. The composition has a "putty-like" consistency and is provided in a sterile, single patient use package.

The tissues used in the bone repair composition are recovered by United States tissue banks, from carefully screened donors, according to standards established by the American Association of Tissue Banks. All such tissues meet stringent specifications during donor screening and laboratory testing in order to reduce the risk of transmitting any infectious disease.

For example, each donor is tested and found to be negative for (at a minimum): hepatitis B surface antigen, human immunodeficiency virus 1 and 2 antibodies, HTLV-1 antibody, hepatitis C virus antibody, and syphilis. The tests were performed by a CLIA approved laboratory utilizing FDA-licensed test kits. The medical and social history of the donor revealed no risk factors for, or clinical evidence of, HIV or hepatitis infection.

This biocompatible composition in accordance with the invention was produced under environmentally controlled conditions using stringent cleaning, preservation, and sterilization procedures. All steps are rigorously quality controlled in accordance with accepted methodologies in the art.

DynaGraft™ Putty is indicated for use in surgical procedures in which osteogenesis, calcification or bony fusion is needed to achieve or enhance the quality of the final result. Accordingly, DynaGraft™ Putty can be used in a variety of orthopedic, reconstructive, and dental bone grafting procedures. DynaGraft™ Putty may be used alone as a bone graft in cases in which the graft is not intended to provide weight bearing support or dimensional integrity to the graft site. If the graft is intended to be weight bearing, the composition should be used with appropriate fixation. DynaGraft™ Putty can, therefore, be used as a complement to musculoskeletal implants such as joint replacement prostheses, intraoral implants, and internal and external fixation devices for procedures in which demineralized freeze-dried bone allograft would be used.

The composition is sterilized by a targeted 2.5 megarads of electron beam irradiation as terminal sterilization. When implanting the composition, sterile technique should be maintained to minimize the risk of post-operative complications. Use of the composition is contraindicated when there is active or latent infection at or near the surgical site.

The composition should be stored long-term in a clean, dry place at room temperature. It should be kept out of direct sunlight and should not be frozen. DynaGraft™ Putty does not require rehydration prior to use.

The packaging of all DynaGraft™ implant compositions has been specially designed to provide ease of use within the surgical field. For example, the composition can be packaged within jars that are kept sterile within one or more foil containers. DynaGraft™ Putty Gel is supplied in 2.5 cc, 5 cc, and 10 cc jars.

To use the composition packaged in jars within foil containers, the packaging is opened by peeling open the outer foil and, using sterile technique, transferring the entire inner package to the sterile field. The inner package is then opened and the jar and a spatula are removed. The jar lid is opened in a sterile manner and composition putty is removed with the spatula or other hand-held instrument.

Appropriate placement of the composition and/or fixation are critical factors in the avoidance of potentially adverse effects on product service life.

Accordingly, the DynaGraft™ Putty is bacteriologically sterile during the stated shelf life in an unopened and undamaged package. The product must be used before the expiration date. Unused product should be properly discarded.

CLOSING

It must be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar to or equivalent to those described herein can be used-in the practice or testing of the invention, the preferred methods and materials are now described. All publications mentioned herein are fully incorporated herein by reference.

What is claimed is:

1. A biocompatible connective tissue repair composition, consisting essentially of:

(a) demineralized bone powder,
   (b) a reverse phase mixture of poloxamer and water,
   wherein the composition exhibits reverse phase behavior and is non-liquid at ambient and body temperatures.

2. The composition of claim 1, wherein the poloxamer is poloxamer 407.

3. The composition of claim 1, wherein the mixture of poloxamer and water is 25 percent weight poloxamer and 75 percent weight water.

4. The composition of claim 1, wherein the composition is 30 percent weight demineralized bone powder and 70 percent weight poloxamer and water.

5. The composition of claim 1, wherein the composition is 50 percent weight demineralized bone powder and 50 percent weight poloxamer and water.

6. The composition of claim 1, wherein the demineralized bone powder is xenogeneic, allogeneic or autogenic.

7. The composition of claim 6, wherein the demineralized bone powder is xenogenic and from a porcine or bovine source.

* * * * *